United States Patent [19]

Sipos

[11] Patent Number: 4,658,056

[45] Date of Patent: Apr. 14, 1987

[54] CATALYTIC OXIDATION OF LIQUID CYCLOPARAFFINS

[75] Inventor: Peter A. Sipos, Kingston, Canada

[73] Assignee: Du Pont Canada Inc., Mississauga, Canada

[21] Appl. No.: 370,928

[22] Filed: Apr. 22, 1982

[30] Foreign Application Priority Data

Apr. 29, 1981 [GB] United Kingdom ............... 8113259

[51] Int. Cl.$^4$ ............... C07C 27/12; C07C 29/50; C07C 45/33; C07C 49/413; C07C 51/31; C07C 61/10; C07C 178/00; C07C 179/053
[52] U.S. Cl. ............... 562/523; 562/529; 562/538; 568/360; 568/570; 568/821; 568/836; 568/838
[58] Field of Search ............... 568/570, 360, 836, 821, 568/838; 562/529, 538, 523

[56] References Cited

U.S. PATENT DOCUMENTS 2,223,494 12/1940 Loder .
2,557,282 6/1951 Hamblet et al. .
2,703,331 3/1955 Goldbeck et al. .
3,530,185 9/1970 Pugi .
3,917,708 11/1975 Kuessner et al. .
3,987,100 10/1976 Barnette et al. .

Primary Examiner—Vivian Garner

[57] ABSTRACT

A process for the catalytic oxidation of liquid cycloparaffins to oxidation products thereof is disclosed. In the process, partial oxidation products are formed by oxidizing the cycloparaffin with molecular oxygen-containing gas in the presence of an oxidation catalyst comprising two heavy metal compounds. The first heavy metal compound is a cobalt compound having ligands selected from dialkyl phosphate, dicycloalkylphosphate and alkylcycloalkylphosphate, optionally additionally combined with pyridine. The second heavy metal compound is a chromium alkanoate. A preferred catalyst is cobalt bis[di(2-ethylhexyl)phosphate] combined with chromium naphthenate.

10 Claims, No Drawings

CATALYTIC OXIDATION OF LIQUID CYCLOPARAFFINS

BACKGROUND

1. Field of the Invention

The present invention relates to a process for the catalytic oxidation of liquid cycloparaffins, especially cyclohexane, in which the oxidation catalyst is a combination of heavy metal compounds. The present invention also relates to an improved process for the manufacture of dicarboxylic acids, especially adipic acid.

2. Description of the Prior Art

The oxidation of cycloparaffins to produce useful partial oxidation products, for example, the oxidation of cyclohexane to cyclohexanol and cyclohexanone, is known as one important step in the manufacture of nylon intermediates, for example, adipic acid. In the case of adipic acid manufacture, it has been found to be preferable to oxidize cyclohexane to adipic acid in a two-step oxidation process, i.e., to oxidize cyclohexane to a mixture containing cyclohexanol and cyclohexanone and to thereafter oxidize that mixture to adipic acid using nitric acid, for example, as described by C. H. Hamblet and A. McAlevy in U.S. Pat. No. 2,557,282, which issued June 19, 1951. Copper and/or vanadium catalysts may be used in the nitric acid oxidation step.

A process in which cyclohexane is oxidized in the liquid phase to cyclohexanol and cyclohexanone at low conversion and high yields was disclosed by D. J. Loder in U.S. Pat. No. 2,223,494, which issued Dec. 3, 1940. In the Loder process, the preferred catalysts include cobalt alkanoate, especially cobalt naphthenate. The yields of cyclohexanol and cyclohexanone obtained by the Loder process were considerably higher than had been achieved in earlier processes not employing catalysts or initiators. While Loder's process when operated on a noncommerical scale, can be made to give yields of cyclohexanol plus cyclohexanone from cyclohexane of 85-95%, in practical commercial operations it is often necessary to compromise on yield in favor of other process parameters in order to have a continuous process which can be run in an economical manner.

It is known that the quantities of useful oxidation products and the by-products of the oxidation of cycloparaffins depend on, in particular, the temperature, residence time, oxygen concentration and flow rates of cycloparaffin, and the like. An improvement in the method for the oxidation of cyclohexane and for the control of the oxidation products so obtained is disclosed by K. Pugi in U.S. Pat. No. 3,530,185, which issued Sept. 22, 1970.

A process for the catalytic oxidation of cycloparaffins to the corresponding cycloalkanol and cycloalkanone in the presence of a catalyst that is, for example, a cobalt monoalkylphosphate and/or cobalt dialkylphosphate, is disclosed by A. Kuessner et al. in U.S. Pat. No. 3,917,708, which issued Nov. 4, 1975. R. A. Zelonka, in U.S. patent application No. 229,873, filed Jan. 30, 1981, now U.S. Pat. No. 4,341,907 discloses a process for the catalytic oxidation of cycloparaffins to the corresponding cycloalkanol and cycloalkanone in the presence of a catalyst that is a cobalt compound in combination with a heterocyclic compound. A process for the preparation of cyclohexanone and cyclohexanol in which cyclohexane is catalytically oxidized in the presence of a binary cobalt/chromium catalyst and subsequently treated to decompose cyclohexylhydroperoxide is disclosed by W. J. Barnette et al. in U.S. Pat. No. 3,987,100, which issued Oct. 19, 1976.

Commercial processes for the oxidation of liquid cycloparaffins are usually operated on such a large scale that there are significant incentives to increase the efficiency of the process, especially with respect to the unit cost, e.g., the cost per ton of product, for the manufacture of useful oxidation products. The percentage yield of useful products, per mole of cycloparaffin oxidized, and the amount of cycloparaffin oxidized, i.e., the conversion obtained as a result of one pass of cycloparaffin through the oxidation zone of the process, are both important process parameters. Such parameters have a major effect on the productivity of the process, i.e., the amount of useful oxidized products formed in the process in a given period of time, which is a prime factor in determining the unit cost for the manufacture of useful oxidation products. In addition, the composition of the oxidation products, e.g., the ratio of cycloalkanol to cycloalkanone, may be an important factor in the efficient operation of processes that convert the useful oxidized products into other products.

It has now been found that cycloparaffins may be catalytically oxidized to useful partial oxidation products, including a relatively high proportion of ketonic oxidation products, by using a process in which the oxidation catalyst is a combination of heavy metal compounds.

SUMMARY OF THE INVENTION

Accordingly, the present invention provides a process for the catalytic oxidation of a liquid cycloparaffin to partial oxidation products thereof, which comprises introducing a molecular oxygen-containing gas into a cycloparaffin of from 5 to 12 carbon atoms at elevated pressure and a temperature of from 130° to 180° C. and in the presence of an oxidation catalyst comprising a combination of a first heavy metal compound and a second heavy metal compound, said oxidation catalyst being soluble in the cycloparaffin, said first heavy metal compound being a cobalt compound having ligands selected from the group consisting of dialkyl phosphate, dicycloalkylphosphate and alkylcycloalkylphosphate, and mixtures thereof, said alkyl group having from 6 to 18 carbon atoms with the proviso that the alkyl group of the dialkylphosphate is a branched alkyl group and said cycloalkyl group has from 5 to 12 carbon atoms, and said second heavy metal compound being a chromium compound having ligands selected from the group consisting of alkanoates having from 6 to 18 carbon atoms, and mixtures thereof, the ratio of cobalt compound to chromium compound being greater than 1:1 on an atomic basis.

In a preferred embodiment of the process of the present invention, the cycloparaffin is cyclohexane or cyclododecane.

In another embodiment, the ligand of the first heavy metal compound is dialkyl phosphate in which the alkyl group is branched in the beta position.

In a further embodiment, the first heavy metal compound of the catalyst is cobalt bis(dialkylphosphate).

In yet another embodiment, the first heavy metal compound is combined with pyridine in addition to being combined with the second metal compound.

In a still further embodiment, free dialkyl phosphate is present in the oxidation catalyst.

In yet another embodiment, the free dialkyl phosphate present in the oxidation catalyst is di(2-ethylhexyl) phosphate.

The present invention also provides a process for the manufacture of dicarboxylic acids by oxidizing with nitric acid the partial oxidation products of the cycloparaffins prepared according to the process of the present invention.

As mentioned above, one embodiment of the present invention relates to the catalytic oxidation of cycloparaffins to form partial oxidation products, especially cycloalkanols and cycloalkanones. The cycloparaffins that may be oxidized according to this embodiment have from 5 to 12 carbon atoms and are, for example, cyclopentane, cyclohexane, cyclooctane and cyclododecane. The preferred cycloparaffin is cyclohexane, the cycloparaffin of greatest industrial importance.

The present invention generally is described hereinafter with reference to cyclohexane as the cycloparaffin.

DETAILED DESCRIPTION

Oxidation, to form partial oxidation products, is effected by contacting cyclohexane with molecular oxygen in the presence of an oxidation catalyst and at a temperature in the range of 130° to 180° C. The preferred operating temperature will depend in particular on whether it is desired to operate the process at relatively low or relatively high levels of productivity, typically relatively low or relatively high levels of conversion of cyclohexane, respectively, to useful oxidation products. The former tend to be operated in a temperature range of about 130° to about 160° C., while the latter tend to be operated in a temperature range of about 160° to about 180° C. Both types of processes are known commercially. In the process of K. Pugi, referred to hereinbefore, liquid cyclohexane is contacted at elevated pressure and normally at a temperature of about 160° to about 180° C., at each of several immediately successive stages of an oxidation zone with a mixture of gases comprising molecular oxygen, at controlled partial pressure, and inert gas. The mixture of gases passes countercurrent to the cyclohexane. The oxidation is usually carried out in the presence of an oxidation catalyst. A stream of cyclohexane containing oxidation products of cyclohexane is recovered from the last of the immediately successive stages.

The pressure at which the process is operated may be varied over a wide range, the actual pressure being governed primarily by other process parameters. Typical operating pressures are in the range 500 to 2500 kPa.

As stated above, oxidation to partial oxidation products is effected by contacting cyclohexane with molecular oxygen in the presence of an oxidation catalyst. The molecular oxygen is preferably introduced in the form of air. The molecular oxygen may, however, be admixed with nitrogen in proportions other than that of air or with other inert gases. Such other inert gases may be any gas or vapor which cannot itself react with cyclohexane or be substantially oxidized under the conditions of the oxidation reaction. Consideration must, however, be given at all times to operating the process of the present invention such that gaseous mixtures formed in the process are not in the explosive range.

The oxidation catalyst of the embodiment of the present invention in which cycloparaffin is oxidized to partial oxidation products thereof is a combination of a first heavy metal compound and a second heavy metal compound. The first heavy metal compound is a cobalt compound having ligands that may be dialkylphosphate, dicycloalkylphosphate or alkylcycloalkylphosphate, or mixtures thereof. Dialkylphosphate ligands are preferred. The alkyl group of the phosphate ligand of the heavy metal compound has 6 to 18 carbon atoms. Preferably, the alkyl group of the dialkylphosphate ligand is a branched alkyl group, especially an alkyl group branched at the beta position. The cycloalkyl group may have from 5 to 12 carbon atoms. The preferred dialkylphosphate ligand is di(2-ethylhexyl) phosphate. The preferred first heavy metal compound is cobalt bis[di(2-ethylhexyl)phosphate].

The second heavy metal compound is a chromium compound having ligands selected from the group consisting of alkanoates having from 6 to 18 carbon atoms, and mixtures thereof. The alkanoate may be derived from straight or branched chain aliphatic acids or from cycloaliphatic acids. The alkanoate preferably has 8 to 12 carbon atoms. In a preferred embodiment the second heavy metal compound is chromium naphthenate.

In addition to being in combination with the second heavy metal compound, the first heavy metal compound may also be in combination with pyridine. In such embodiments the relative amounts of pyridine and first heavy metal compound may be varied over a wide range, for example, at ratios of from 1:1 to 20:1, a preferred ratio being about 4:1 (molar basis).

The oxidation catalyst is preferably prepared, usually in the cycloparaffin to be oxidized, by premixing the components or by admixing the components immediately prior to feeding the resultant catalyst to the oxidation zone. It is preferred that the mixing occurs before the oxidation catalyst is fed to the oxidation zone in order to facilitate the interaction, and any resultant "complex" formation that may occur in the solution between the first and second heavy metal compounds, and pyridine if present. Admixing after entering the oxidation zone tends to be less effective because of dilution effects.

The relative amounts of first heavy metal compound and second heavy metal compound may be varied over a wide range, for example, using ratios of cobalt: chromium in the range of 10:1 to 1:1 on an atomic basis. However at the low ratios, i.e., relatively high amounts of chromium, the oxidation reactor may show an increased tendency for fouling, i.e., the formation of deposits within the reactor. This tendency for fouling may be reduced provided that free dialkyl phosphate, i.e., dialkyl phosphate and especially di(2-ethylhexyl)phosphate, in addition to any which may be combined with the cobalt as a ligand, is added to the catalyst solution.

The oxidation catalyst fed to the oxidation zone in the partial oxidation step must be soluble in the cycloparaffin, e.g., cyclohexane, at the temperature of the cycloparaffin in the zone. For practical reasons, the oxidation catalyst is usually formed at temperatures below the temperature of the oxidation zone, especially at temperatures near 25° C. Thus, the oxidation catalyst is preferably soluble in the cycloparaffin at temperatures of from about 25° C. to at least that of the oxidation zone.

The concentration of catalyst may be varied over a wide range, for example, from 0.1 to 10 ppm of combined heavy metals in the catalyst fed to the oxidation zone. As will be appreciated by those skilled in the art, the catalyst is normally initially formed at temperatures well below that of the oxidation zone as a concentrate in hydrocarbon, for example, with heavy metal concentrations of at least 0.1%, especially at least 1%, and then admixed with the hydrocarbon being oxidized. Catalysts capable of being formed into such concentrates are regarded as catalysts that are soluble in the hydrocarbon being oxidized.

The oxidation products of the process of the present invention are normally subjected to further processing steps, e.g., so as to obtain adipic acid if the cycloparaffin is cyclohexane, as is known in the art. One such further processing step may be a preparatory treatment step, prior to further oxidation to adipic acid, known as a "wet KA" process, which was disclosed by M. Goldbeck, Jr., et al. in U.S. Pat. No. 2,703,331, which issued Mar. 1, 1955. In that process, an oil distillate is first obtained by injecting water into the partial oxidation products leaving the oxidation zone. Hydrocarbon and aqueous phases are then separated from the resulting mixtures and steam-distillable oil is removed from the aqueous phase. The oil is added to the hydrocarbon phase whereupon substantially all of the hydrocarbon is stripped therefrom and the residue steam-distilled to provide a suitable feed for a nitric acid oxidation process. The presence of water is advantageous during the recovery of cyclohexane from the partial oxidation products because it suppresses dehydration of cyclohexanol and cyclohexanone to such products as cyclohexylidene cyclohexanone, cyclohexyl ethers and cyclohexyl esters.

As disclosed hereinabove, the oxidation of partial oxidation products of cyclohexane to adipic acid is known in the art. In particular, the admixture of partial oxidation products, especially in the form obtained from a so-called "wet KA" process, are fed to a nitric acid oxidation process. The nitric acid oxidation may be carried out in two stages, operated at different temperatures, using nitric acid at a concentration of 30–70%. Typical temperatures are 40°–90° C. in the first stage and 90°–120° C. in the second stage. Catalysts may be used in the nitric acid oxidation process, especially copper and/or vanadium catalysts, examples of which are copper nitrate or sulphate and sodium or ammonium vanadate.

In an embodiment of the present invention, the partial oxidation products of cycloparaffin, especially cyclohexane, fed to a nitric acid oxidation process for the manufacture of dicarboxylic acid, especially adipic acid, are derived from the oxidation of the cycloparaffin in the manner described hereinabove. Such oxidation products contain a relatively high proportion of ketonic oxidation products in comparison with partial oxidation products obtained from the cycloparaffin with, for example, cobalt naphthenate as the sole catalyst. Ketonic oxidation products, for example, cyclohexanone, represent a more advanced stage in the oxidation of the cycloparaffin than do the corresponding alcohols, for example, cyclohexanol. Thus the relatively high proportion of ketonic oxidation products offers the opportunity to manufacture dicarboxylic acids containing a higher proportion of the desired product.

The present invention may be used in the manufacture of partial oxidation products of cycloparaffins and especially in the manufacture of dicarboxylic acids from cycloparaffins. In particular, the invention is useful in the manufacture of adipic acid from cyclohexane.

The present invention is illustrated by the following examples.

EXAMPLE I

Cyclohexane was fed on a continuous basis to a stirred one-liter reactor. The volume of liquid in the reactor was controlled at approximately 450 ml. In the reactor the cyclohexane was maintained at a temperature of 170° C. and under a pressure of 1190 kPa. Molecular oxygen in the form of air was fed to the reactor at a rate of 181 liters, at 21° C. and atmospheric pressure, per hour. Oxidation catalyst, in cyclohexane solution, was also fed to the reactor on a continuous basis. The residence time in the reactor was 10 minutes.

The streams containing cyclohexane and its partial oxidation products that passed from the reactor were collected for a period of one hour and then analyzed using gas chromatographic and coulometer techniques. Gaseous products were also analyzed. In addition, samples of the partial oxidation products were further oxidized, using nitric acid, to the corresponding dicarboxylic acids.

Further process details and the results obtained are given in Table I.

The results given in Table I, and in the Examples that follow, are average results for at least three consecutive one-hour tared runs.

The runs of Table I show that Run 1 and Run 2 of the present invention resulted in a higher proportion of ketonic oxidation products than the comparative Runs 3, 5 and 6, and a substantially higher productivity than comparative Run 4. In addition, a high yield of adipic acid was achieved in Runs 1 and 2 with relatively low production of cyclohexylhydroperoxide compared with the result obtained with comparative Runs 3 and 5. Low levels of cyclohexylhydroperoxide are desirable, especially in partial oxidation products as fed to a nitric acid oxidation process, for safety reasons.

EXAMPLE II

The procedure of Example I was repeated using a catalyst that contained cobalt bis[di(2-ethylhexyl)phosphate] in combination with pyridine. The results obtained are given in Table I.

The results show that a similar yield of adipic acid was obtained in Run 7 with substantially higher proportion of ketonic oxidation product and at a substantially lower level of cyclohexylhydroperoxide compared with the comparative Run 8.

TABLE I

| Run No. | 1 | 2 | 3 | 4 | 5 | 6 | 7 | 8 |
|---|---|---|---|---|---|---|---|---|
| Catalyst* | CA/CB | CA/CB | CA | CB | CC | CC/CB | CD/CB | CD |
| Catalyst Concentration in Reactor Feed (ppm of metal) | 2.8/1.4 | 2.0/0.5 | 1.4 | 1.4 | 1.4 | 2.0/0.5 | 1.7/0.8 | 1.4 |
| Cobalt/Chromium (atomic ratio) | 1.76 | 3.52 | | | | 3.52 | 1.87 | |
| Cyclohexane Conversion (%) | 3.96 | 3.83 | 4.17 | 3.83 | 4.15 | 3.78 | 3.89 | 4.18 |
| Productivity** (KAP, g/hour) | 82.1 | 80.4 | 91.2 | 76.2 | 87.1 | 80.4 | 81.3 | 90.9 |
| Yield (%)** | | | | | | | | |

TABLE I-continued

| Run No. | 1 | 2 | 3 | 4 | 5 | 6 | 7 | 8 |
|---|---|---|---|---|---|---|---|---|
| K | 36.1 | 35.6 | 20.3 | 38.6 | 23.2 | 33.3 | 36.6 | 22.0 |
| A | 27.5 | 28.4 | 34.1 | 26.1 | 37.6 | 34.9 | 29.7 | 38.7 |
| P | 5.9 | 6.4 | 16.8 | 2.5 | 9.0 | 3.3 | 4.3 | 11.0 |
| D | 1.0 | 1.0 | 1.1 | 1.0 | 1.3 | 1.3 | 1.3 | 1.4 |
| KA | 63.7 | 64.1 | 54.4 | 64.8 | 60.9 | 68.2 | 66.3 | 60.7 |
| KAPD | 70.7 | 71.5 | 72.2 | 68.3 | 71.2 | 72.9 | 71.9 | 73.1 |
| Adipic Acid | 67.5 | 68.9 | 68.4 | 67.8 | 67.7 | 69.0 | 68.0 | 68.2 |
| Ratio of A:K | 0.78 | 0.80 | 1.68 | 0.69 | 1.65 | 1.05 | 0.83 | 1.79 |

*CA = Cobalt bis[di(2-ethylhexyl)phosphate].
CB = Chromium naphthenate.
CC = Cobalt bis-(2-ethylhexanote).
*CD = Cobalt bis[di(2-ethylhexyl)phosphate] in combination with pyridine at a ratio of 1:4 (molar basis).
**K = cyclohexanone.
A = cycloyhexanol.
P = cyclohexylhydroperoxide.
D = dicyclohexylhydroperoxide.
N.B. KAP represents the sum of K, A and P. KAPD represents the sum of K, A, P and D.
Runs 3, 4, 5, 6, and 8 are comparative runs and are not of the present invention.

I claim:

1. A process for the catalytic oxidation of a liquid cycloparaffin to partial oxidation products thereof, which comprises introducing a molecular oxygen-containing gas into a cycloparaffin of from 5 to 12 carbon atoms at elevated pressure and a temperature of from 130° to 180° C. and in the presence of an oxidation catalyst comprising a combination of a cobalt compound and a chromium compound, said oxidation catalyst being soluble in the cycloparaffin, said cobalt compound having ligands selected from the group consisting of dialkyl phosphate, dicycloalkylphosphate and alkylcycloalkylphosphate, and mixtures thereof, said alkyl group having from 6 to 18 carbon atoms with the proviso that the alkyl group of the dialkylphosphate is a branched alkyl group and said cycloalkyl group has from 5 to 12 carbon atoms, and said chromium compound having ligands selected from the group consisting of alkanoates having from 6 to 18 carbon atoms, and mixtures thereof, the ratio of cobalt compound to chromium compound being greater than 1:1 on an atomic basis, said catalyst also containing free dialkylphosphate.

2. The process of claim 1 in which the partial oxidation products are selected from the group consisting of cycloalkanols, cycloalkanones and cycloalkylhydroperoxides, and mixtures thereof.

3. The process of claim 1 in which the cycloparaffin is cyclohexane.

4. The process of claim 1 in which the cycloparaffin is cyclododecane.

5. The process of claim 1 in which the ligand of the cobalt compound is dialkylphosphate in which the alkyl group is branched in the beta position.

6. The process of claim 5 in which the cobalt compound is cobalt bis[di(2-ethylhexyl)phosphate].

7. The process of claim 1 in which the cobalt compound is in combination with pyridine.

8. The process of claim 1 in which the chromium compound is chromium naphthenate.

9. The process of claim 1, claim 6 or claim 8 in which free di(2-ethylhexyl)phosphate is present in the oxidation catalyst.

10. The process of claim 1 wherein the partial oxidation products are oxidized with nitric acid to the corresponding dicarboxylic acid.

* * * * *